US010869642B2

United States Patent
Nempont et al.

(10) Patent No.: US 10,869,642 B2
(45) Date of Patent: Dec. 22, 2020

(54) AUTOMATIC MOVEMENT DETECTION

(71) Applicant: KONINKLIJKE PHILIPS N.V., Eindhoven (NL)

(72) Inventors: Olivier Pierre Nempont, Suresnes (FR); Guillaume Julien Joseph Pizaine, Issy-les-Moulineaux (FR); Raoul Florent, Ville d'Avray (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 548 days.

(21) Appl. No.: 15/557,855

(22) PCT Filed: Mar. 2, 2016

(86) PCT No.: PCT/EP2016/054345
§ 371 (c)(1),
(2) Date: Sep. 13, 2017

(87) PCT Pub. No.: WO2016/146380
PCT Pub. Date: Sep. 22, 2016

(65) Prior Publication Data
US 2018/0055462 A1    Mar. 1, 2018

(30) Foreign Application Priority Data
Mar. 16, 2015 (EP) .................................... 15305383

(51) Int. Cl.
*A61B 6/12* (2006.01)
*A61B 6/00* (2006.01)
(Continued)

(52) U.S. Cl.
CPC ............... *A61B 6/12* (2013.01); *A61B 6/461* (2013.01); *A61B 6/487* (2013.01); *A61B 6/504* (2013.01);
(Continued)

(58) Field of Classification Search
CPC ... A61M 2025/09166; G06K 2209/057; G06T 7/246; G06T 7/0012; G06T 2207/10016;
(Continued)

(56) References Cited

U.S. PATENT DOCUMENTS 5,274,551 A * 12/1993 Corby, Jr. ............... A61B 6/463
348/45
6,320,976 B1 * 11/2001 Murthy ................ A61B 5/0002
382/128
(Continued)

FOREIGN PATENT DOCUMENTS

| EP | 0545588 A2 | 6/1993 |
| WO | 2004034329 A2 | 6/2000 |
| WO | 2011039681 A1 | 4/2011 |

OTHER PUBLICATIONS

Cui ["Temporal Spectral Residual for fast salient motion detection" Neurocomputing 86 (2012) 24-32]. (Year: 2012).*
(Continued)

*Primary Examiner* — Oommen Jacob

(57) ABSTRACT

A method and device is proposed for automatic detection of an event in which a device is leaving a stable position relative to and within an anatomy. The method comprises the steps of receiving a sequence of fluoroscopic images, detecting a device in at least two of the fluoroscopic images, determining a motion field of the detected device in the sequence of fluoroscopic images, generating a sequence of integrated images by integrating the sequence of fluoroscopic images taking into consideration the motion field, determining a saliency metric based on the integrated images, identifying a landmark in the integrated images based on the saliency metric, and determining as to whether the landmark is moving relative to the device, based on a variation of the saliency metric.

12 Claims, 5 Drawing Sheets

(51) Int. Cl.
  *G06T 7/246* (2017.01)
  *A61B 34/20* (2016.01)
  *G06T 7/00* (2017.01)
  *A61B 90/00* (2016.01)
  *A61M 25/09* (2006.01)

(52) U.S. Cl.
  CPC ............ *A61B 34/20* (2016.02); *G06T 7/0012* (2013.01); *G06T 7/246* (2017.01); *A61B 2034/2065* (2016.02); *A61B 2090/363* (2016.02); *A61M 2025/09166* (2013.01); *G06K 2209/057* (2013.01); *G06T 2207/10016* (2013.01); *G06T 2207/10121* (2013.01); *G06T 2207/30021* (2013.01); *G06T 2207/30104* (2013.01)

(58) Field of Classification Search
  CPC . G06T 2207/30021; G06T 2207/10121; G06T 2207/30104; A61B 6/12; A61B 6/461; A61B 34/20; A61B 6/487; A61B 6/504; A61B 2034/2065; A61B 2090/363
  USPC .................................................. 600/427, 407
  See application file for complete search history.

(56) References Cited

U.S. PATENT DOCUMENTS

| | | | | |
|---|---|---|---|---|
| 7,609,814 B2* | 10/2009 | Baumgart | ............... | A61B 6/463 378/62 |
| 8,111,895 B2* | 2/2012 | Spahn | ................ | G06T 5/50 378/5 |
| 8,600,538 B2* | 12/2013 | Holroyd | ................ | B29C 65/002 700/119 |
| 8,712,177 B2* | 4/2014 | Liao | ................ | G06T 11/60 382/254 |
| 9,147,255 B1* | 9/2015 | Zhang | ................ | G06T 7/162 |
| 2005/0171420 A1* | 8/2005 | Boese | ................ | A61B 5/721 600/407 |
| 2006/0251300 A1 | 11/2006 | Borgert | | |
| 2008/0027316 A1* | 1/2008 | Baumgart | ............... | A61B 6/463 600/425 |
| 2008/0101670 A1* | 5/2008 | Baumgart | ................ | G06T 5/50 382/128 |
| 2008/0137935 A1* | 6/2008 | Spahn | ................ | G06T 5/50 382/132 |
| 2011/0164035 A1 | 7/2011 | Liao | | |
| 2011/0170599 A1* | 7/2011 | Francois | ............... | H04N 19/105 375/240.16 |
| 2012/0059253 A1* | 3/2012 | Wang | ................ | A61B 6/00 600/427 |
| 2012/0183189 A1* | 7/2012 | Florent | ................ | A61B 6/02 382/128 |
| 2012/0255663 A1* | 10/2012 | Holroyd | ................ | B29C 65/002 156/64 |
| 2013/0050574 A1* | 2/2013 | Lu | ................ | G06K 9/00751 348/441 |
| 2013/0331687 A1 | 12/2013 | Liao | | |
| 2014/0112438 A1 | 4/2014 | Mountney | | |
| 2015/0055824 A1* | 2/2015 | Hong | ................ | G06K 9/00624 382/103 |
| 2018/0055462 A1* | 3/2018 | Nempont | ................ | G06T 7/246 |

OTHER PUBLICATIONS

Color Expert ADmin ["Photo Masking Tutorial: Extract a Photo"], Oct. 17, 2012 (Year: 2012).*

Ross, James C. et al "Registration and Integration for Fluoroscopy Device Enhancement", MICCAI, 2005, vol. 3749, pp. 851-468.

Dvir, Danny et al "Transcatheter aortic valve implantation of a CoreValve device using novel real-time imaging guidance", Cardiovascular Revascularization Medicine, 2011.

"What Is Image Masking? Why Do You Need It?" Published by Color Experts International, Inc, on Mar. 14, 2016, Downloaded From https:www.colorexpertsbd.com/blog/what-is-image-masking, 5 Page Document.

* cited by examiner

AUTOMATIC MOVEMENT DETECTION

CROSS-REFERENCE TO PRIOR APPLICATIONS

This application is the U.S. National Phase application under 35 U.S.C. § 371 of International Application No. PCT/EP2016/054345, filed on Mar. 2, 2016, which claims the benefit of European Patent Application No. 15305383.0, filed on Mar. 16, 2015. These applications are hereby incorporated by reference herein.

FIELD OF THE INVENTION

The present invention relates to method of and system for automatic detection of an event in which a device is leaving a stable position relative to and within an anatomy. In other words, the invention relates to method of and system for automatic detection of movement of a device relative to and within an anatomy. Furthermore, the invention relates to a corresponding computer program.

BACKGROUND OF THE INVENTION

The navigation and precise positioning of a guidewire and of interventional devices is tedious, time-consuming, and requires additional contrast agent bursts to clarify the position of the devices relative to the relevant vessels. Due to scatter, both patient and medical staffs are exposed to x-ray during the acquisition of diagnostic angiograms and interventional fluoroscopy. Navigation support is desired to reduce the intervention time and to enhance the positioning accuracy.

3D roadmapping is thus of importance in many interventions under X-ray guidance. Since the vascular anatomy is almost not visible in fluoroscopic images without the injection of a contrast agent, a registered (either statically or dynamically) 3D roadmap provides an interventionists with a visual reference for various tasks such as navigation, positioning or deploying a device and/or assessment of the outcome.

Static motion compensation involves registering the 3D roadmap to find a single geometric transformation for the entire fluoroscopic sequence, whereas dynamic motion compensation requires finding the right geometric transformation for each frame in the sequence.

There are two ways to achieve dynamic motion compensation. The first approach consists in tracking anatomical landmarks connected to the vascular anatomy, having the same motion as the vessels, as for example in the context of valve positioning and deployment during a TAVI procedure.

The second approach consists in tracking a device connected to the vascular anatomy and thus having a similar motion. Devices are clearly visible and are good candidates for dynamic motion compensation algorithms.

Both approaches have disadvantages:
Anatomical landmarks are often very faint and cluttered with opaque objects, so tracking them is a very tough task. Additionally, detecting and tracking such landmarks requires additional inputs from the user.
Locking interventional devices inside vessels is part of the protocol and has to be enforced, at best. If a prosthesis or a stent is to be deployed, the device may even be pulled back completely. Device unlocking is thus common and must be detected to assess the validity of motion compensation.

Furthermore, a navigation system can help the cardiologists by providing a cardiac roadmap displayed next or overlaid on the live fluoroscopy pictures. Ideally, this cardiac roadmap represents the vessel network acquired during angiography.

WO 2011/039681 A1 describes a method and a medical imaging system for accurate positioning for vessel intervention procedures. First, at least one x-ray image of a vessel region of interest is acquired with injected contrast agent. Further, vessel information data is identified within the at least one acquired image. Then, first calcification features of the vessel in the vessel region of interest in the at least one acquired image are detected. Further, vessel representation is generated using the vessel information data and the detected calcification features. Further, at least one current fluoroscopic image of the vessel region of interest is acquired. Then, second calcification features of the vessel in the vessel region of interest in the at least one current fluoroscopic image are detected, wherein the second calcification features are according to the first calcification features. Further, the vessel representation is registered with the fluoroscopic image, wherein the calcification features are used for the registration. Then, a composite image is generated by combining the vessel representation with the at least one fluoroscopic image. The composite image is finally displayed.

In WO 2004/034329 A2, there is described a basic method for realizing cardiac roadmapping, relying on the extraction of the cardiac and respiratory cycles, and on the matching of those cycles between the angiogram images (in filled state) and the live images.

SUMMARY OF THE INVENTION

The present invention suggests the presence of both the device and the anatomical landmarks. Particularly, a method is proposed for automatic device unlocking detection using anatomical landmarks which, coupled with device-based motion compensation, makes it possible to design a fully automatic dynamic motion compensation approach.

It can be seen as an object of the invention to provide a method and device eliminating or at least reducing the above mentioned drawbacks.

It is a further object of the invention to provide for an indication of a movement of an instrument in and relative to an anatomy part.

This is achieved by the subject matter of each of the respective independent claims. Further embodiments are described in the respective dependent claims.

Generally, a method for automatic detection of an event in which a device is leaving a stable position relative to and within an anatomy comprises the steps of receiving a sequence of fluoroscopic images, detecting a device in at least two of the fluoroscopic images, determining a motion field of the detected device in the sequence of fluoroscopic images, generating a sequence of integrated images by integrating the sequence of fluoroscopic images taking into consideration the motion field, determining a saliency metric based on the integrated images, and identifying a landmark in the integrated images based on the saliency metric. Further, it may be determined as to whether the landmark is moving relative to the device, based on a variation of the saliency metric.

It is noted that a device or a portion of interest of a device may be detected in a fluoroscopy image manually or by means of automatic procedures utilizing appropriate image processing computer software. Based on such detection, also the area surrounding the portion of the instrument may be defined manually by for example input, or may be defined automatically according to a previously determined procedure or software algorithms. It will be understood that a definition of an area may be performed automatically after a portion of a device is detected manually, or the area may be defined manually after the system has detected aspects in a fluoroscopy image including a device, and supposed a portion by for example high-lighting the same.

In the context of the described method, a device may be an interventional instrument which can be introduced into a body for therapeutic or diagnostic purposes, for example a catheter for insertion of a stent into a vasculature. A portion of interest of such a device may particularly be a tip portion of the device, i.e. a distal end portion of a device, for example a distal portion of a catheter at which a stent is accommodated for introduction into a body. For example, the instrument may be, on the one hand, a flexible or stiff catheter or wire tip or an electrode, and on the other hand also a biopsy device, a cannula or trocar. It can also be an endoprothesis such as a stent, an occluder (e.g. a Patent Foramen Oval occluder), an artificial valve, etc. . . .

It will be understood that a motion field is a mathematical function which give the motion of pixels, from a given image to another one. For instance, the motion field of the pigtail catheter indicates how and how much to displace the pigtail from its position in the current frame, to find its position in the next frame. In other words, a sequence of fluoroscopic images comprises a first fluoroscopic image and a second fluoroscopic image, and a determination of a motion field comprises a determination of a displacement of for example a device between a position detected in the first fluoroscopic image and a position detected in the second fluoroscopic image. A motion field may consequently comprise displacements of a plurality of pixels related to one device. In the described method, a displacement of at least one pixel related to a device may be taken into consideration for integrating the plurality of, i.e. the at least two fluoroscopic images.

It is further noted that the term saliency metric refers to a quantitative measure which allows highlighting regions having a desired property in the image. A saliency metric may be a map, computed from the integrated image, wherein the higher a pixel value, the more likely this pixel belongs to a structure having the same motion than the device. Structures are "salient" given a property. Here, this property is "having the same motion or displacement as the device". In other words, the term saliency metric refers to a map including at least one salient structure which salient structure may be denoted as landmark. A landmark and in particular an anatomical landmark like a calcification is determined in an integrated image based on the height of pixel values.

The aim of the invention is to take advantage of the motion field of the device to enhance such structures or landmarks, which would be too faint to be detectable otherwise.

According to an embodiment of the method, the integration of the sequence of fluoroscopic images is a temporal integration. That is, the received sequence of fluoroscopic images is processed, i.e. integrated in accordance with the sequence in time in which these fluoroscopic images have been generated.

In a sequence of more than two integrated images, the saliency metric may be newly determined for each newly received integrated image so that a sequence of saliency metrics is generated. In such a sequence, the saliency metric may vary when comparing pixel values of landmarks in one saliency metric with another saliency metric. For example, when a pixel value of a landmark increases from one saliency metric to the next one, it is likely that the device is not displaced relative to the landmark. On the other hand, when a pixel value of a landmark decreases from one saliency metric to the next saliency metric, it can be assumed that the device is moving relative to the landmark.

According to an embodiment, the method may further comprise the step of visualizing at least one fluoroscopic image out of the sequence of fluoroscopic images together with a roadmap as an overlay of the roadmap on the at least one fluoroscopic image.

The roadmap may be masked when a motion of the landmark relative to the device (or vice versa) is determined as described above.

It is noted that an anatomical landmark may include a calcification in a vascular system. Otherwise, a landmark may also include an already implanted element like a stent or any other surgical implant or orthopedic implant which is already implanted in the vicinity of the device introduced into the vasculature.

If calcifications are pre-segmented from a preoperative 3D CT volume, they can be projected on the 2D sequence in real-time. Their 2D shape and appearance are thus known and can be used to improve the saliency metric.

If calcifications are pre-segmented from a preoperative 3D CT volume, their projection on the 2D sequence may be used to refine the region where temporal integration is performed.

The region where the saliency metric is computed can be narrowed down by detecting and masking other devices first (e.g. the prosthetic aortic valve).

To ensure dynamic motion compensation throughout the deployment, detecting unlocking (and thus failure) may trigger an alternative to the current tracking algorithm, e.g. calcifications tracking.

According to another aspect of the invention, a system for automatic detection of an event in which a device is leaving a stable position relative to and within an anatomy comprises, in general, a device for generating fluoroscopic images, and a processing device for processing the fluoroscopy images in accordance with the above described method.

The system may further comprise a database providing at least one roadmap.

The result of the method, i.e. the achieved combined images, may be displayed on a suitable device, for example on a monitor.

According to a further aspect, computer program is provided for automatic detection of an event in which a device is leaving a stable position relative to and within an anatomy, wherein the computer program, when being executed on a processing device of a system, causes the system to perform the above described method.

Therefore, the method according to the invention may be performed substantially automatically, or at least predominantly automatically. Therefore, the computer program may comprise sets of instructions for gathering and at least temporarily storing at least two fluoroscopic images generated by an appropriate system, sets of instructions for identifying a device shown in the fluoroscopy images, sets of instructions for determining a motion field of the detected device in the fluoroscopic images, sets of instructions for integrating the fluoroscopic images based on the motion field, sets of instructions for determining a saliency metric based on the integrated images, sets of instructions for identifying a landmark in the integrated images based on the saliency metric, and sets of instructions for determining as to whether the landmark is moving relative to the device, based on a variation of the saliency metric.

Further, the computer program may comprise sets of instructions for loading data from a data base including previously recorded image information, or may comprise sets of instructions for information retrieval from a user.

Such a computer program is preferably loaded into a work memory of a data processor. The data processor is thus equipped to carry out the method of the invention. Further, the invention relates to a computer readable medium, such as a CD-ROM, at which the computer program may be stored. However, the computer program may also be presented over a network like the World Wide Web and can be downloaded into the work memory of a data processor from such a network.

It has to be noted that embodiments of the invention are described with reference to different subject matters. In particular, some embodiments are described with reference to method type claims whereas other embodiments are described with reference to apparatus type claims. However, a person skilled in the art will gather from the above and the following description that, unless other notified, in addition to any combination of features belonging to one type of subject matter also any combination between features relating to different subject matters is considered to be disclosed with this application.

The aspects defined above and further aspects, features and advantages of the present invention can also be derived from the examples of the embodiments to be described herein after and are explained with reference to examples of embodiments also shown in the figures, but to which the invention is not limited.

DETAILED DESCRIPTION OF EMBODIMENTS

Figure 1:
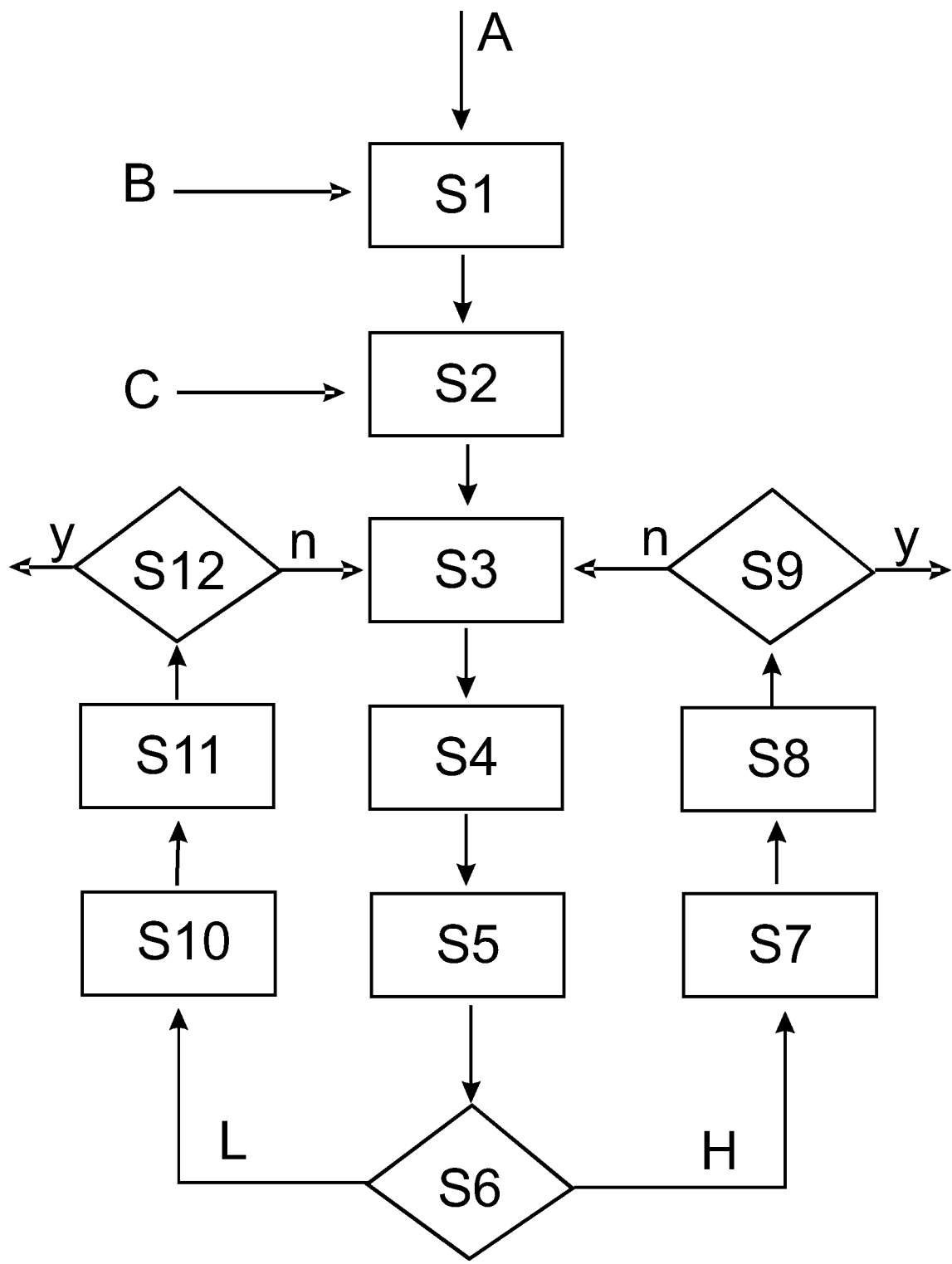
FIG. 1 is a flowchart illustrating a method according to the invention.

The flowchart in FIG. 1 illustrates the principle of a method according to the invention. It will be understood that the steps described with respect to the method are major steps, wherein these major steps might be differentiated or divided into several sub steps. Furthermore, there might be also sub steps between these major steps. Therefore, a sub step is only mentioned if that step is important for the understanding of the principles of the method according to the invention.

By way of example, a TAVI procedure is considered in the following, where dynamic motion compensation is particularly useful during valve positioning and valve deployment.

Patients undergoing TAVI interventions usually have calcified aorta and/or coronary arteries. Provided these calcifications are close enough to the aortic root, they may serve as anatomical landmarks.

Diagnosis and intervention planning are based on diagnostic angiograms. After a catheter is inserted into the vascular system at an access site, it is advanced along large vessels to the vascular structure that requires treatment. Contrast agent is injected via the catheter and cathlab x-ray equipment records an angiographic sequence that shows the vessels when filled with contrast agent. The diagnostic angiogram acquisitions can be repeated with varying imager geometries.

During a following intervention, a flexible, partially or fully radio-opaque guidewire is advanced to the affected vascular structures (e.g. stenoses in coronaries, neurovascular aneurisms, or arterio-venous malformations). Fluoroscopic low-dose x-ray surveillance visualizes the guidewire and allows for the hand-eye-coordination of the interventionalist while advancing the guidewire. When positioned, the guidewire serves as rail to deliver interventional devices (e.g. balloons for dilation and stent delivery, detachable coils for aneurysm clotting). The delivery and deployment of the interventional devices is also fluoroscopy-controlled.

The interventionist may lock the catheter on to a cusp of the aorta. As an input, it may be assumed that the aortic root has been segmented in a preoperative 3D CT volume (input A to step S1 in FIG. 1). Further, an angiogram or a plurality of angiograms is provided by an x-ray imaging system of the region of interest (input B to step S1 in FIG. 1).

In step S1, a 3D roadmap of the aortic root may be statically registered to a previous angiogram. Then, the interventionist acquires a fluoroscopic sequence with the same geometry parameters than the angiogram, so that the registration of the 3D roadmap is still valid (input C to step S2 in FIG. 1).

In step S2, the signature of the injection catheter in the 2D X-ray sequence is detected. That is, the catheter is identified in at least two of the x-ray images or frames.

In step S3, the catheter is tracked in the sequence of x-ray/fluoroscopic images so that a displacement field or motion field is obtained for a current frame.

In step S4, in a region where the anatomical landmarks are expected to appear, the motion field is used to compensate for various motions (heartbeat, breathing . . . ). In the motion-compensated region, a temporal integration of the signal is performed. As a consequence, every anatomical structures having the same motion than the device will be at the same location, so their signal will be enhanced by temporal integration. On the contrary, temporal integration will mix up objects or anatomical structures having different motions, so they will appear as blurred regions.

A saliency metric is then computed from the integrated region in step S5, with high values indicating that anatomical structures have been enhanced and low values indicate that anatomical structures have been blurred out.

In step S6, it is determined as to whether the values are high or low. In case of high values (path H in FIG. 1), the device and the anatomical landmarks follow the same displacement/motion field, which means that the device is still locked on to the aortic root and the method proceeds with step S7. In case of low values (path L in FIG. 1), the at least one anatomical landmarks have a motion which is not identical to the device motion, so that it can be concluded that the device is unlocked. In this case the method will proceed with step S10.

In step S7, an overlay technique of the angiogram into the live images (referred to as roadmapping) is utilized, as the vessel structure itself is not radio-opaque, i.e. not visible during the intervention. A static diagnostic angiogram acquired with a similar imager geometry may be displayed next to the live interventional fluoroscopy. For the navigation of guidewire and devices within the vessels, a subjective visual fusion of the static angiogram and the live fluoroscopy is advantageous. An improved context-rich visualization could give important support in navigation. Therefore, at least outlines of preprocessed angiograms are overlaid onto the fluoroscopic image stream so that vessels and the interventional devices are synchronously displayed on one screen.

In step S8, a saliency metric may be displayed, i.e. a map may be displayed in which at least one landmark in the vicinity of the device is indicated. The appropriate saliency metric serves as a visual feedback to an interventionist, showing enhanced anatomical structures when the device is locked. It is noted that step S8 may also be omitted.

In step S9, it is checked as to whether the currently processed fluoroscopic frame is the last frame. If yes (y), the procedure is done, if no (n), the procedure repeats step S3 by tracking the device in the next frame.

Should the value have been determined in step S6 as being low, i.e. unlocking has been detected, the display of the 3D roadmap is turned off in step S10, and a visual warning can be issued in step S11.

Like in step S9, it is checked in step S12 as to whether the currently processed fluoroscopic frame is the last frame. If yes (y), the procedure is done, if no (n), the procedure repeats step S3 by tracking the device in the next frame.

Figure 2:
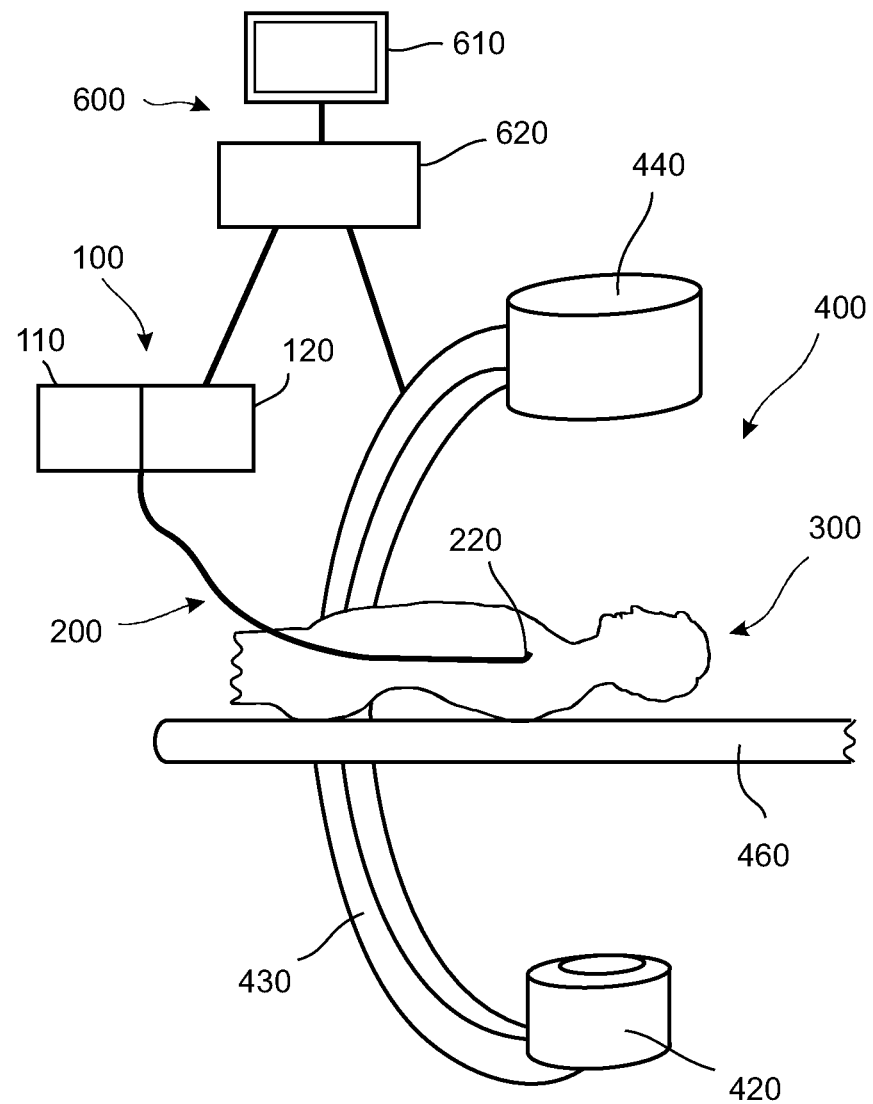
FIG. 2 shows an example of a system according to the invention.

FIG. 2 shows an exemplary system according to the invention, the system including a console 100 for an instrument 200, which instrument may be introduced into a patient 300. Furthermore, an x-ray device 400 is arranged relative to the patient such that a fluoroscopy image of a region may be generated in which the tip portion 220 of the instrument 200 is located. Finally, a processing unit 600 is provided which may control the generating of the fluoroscopy image by means of the x-ray device 400, as well as the console 100 to control functions of the instrument 200, if appropriate.

Here, the controller 100 may also include a unit 110 by means of which a contrast agent may be delivered, so that e.g. an angiography image or a series of angiography images may be generated. On the other hand, by way of the unit 110, drugs may be injected. Further, the console 100 may comprise a device 120 by means of which for example the orientation of the tip portion 220 of the instrument 200 may be controlled, or which may control special functions of the instrument like laser application or a placing of a prosthesis like a stent, or introducing and inflating a balloon. It is noted that the console 100 may include also more than two units or devices, depending on the intended treatment.

The x-ray device 400 includes an x-ray source 420 as well as a detector for x-ray radiation 440, wherein both, the x-ray source 420 as well as the x-ray detector 440 are arranged at a C-arm 430 to ensure a proper orientation of both, relative to each other. The patient 300 may be positioned at a table 460.

The processing unit 600 includes first of all a control unit 620 and further a monitor 610, wherein an output of information with respect to the current location of for example a tip of an instrument may be shown on said monitor.

The processing unit 600 may further comprise a processing device or working memory on which a computer program to perform the unlock detection according to the invention, may be stored and/or executed.

Figure 3:
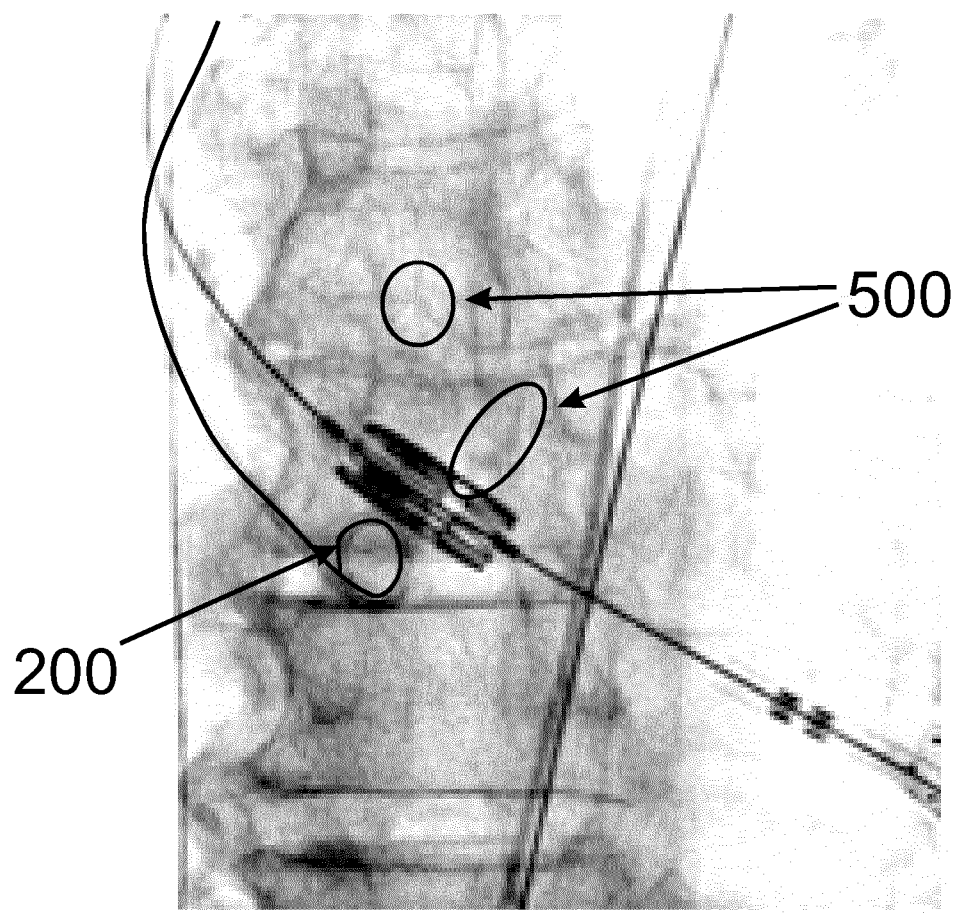
FIG. 3 shows an example of a fluoroscopy image with highlighted landmarks.

FIG. 3 shows an example of a fluoroscopy image showing on the one hand a distal end portion of a device/catheter 200, here in particular a collapsed stent-based heart valve on a catheter, and on the other hand calcifications 500 which may be used as anatomical landmarks in a method as illustrated in FIG. 1.

Figure 4:
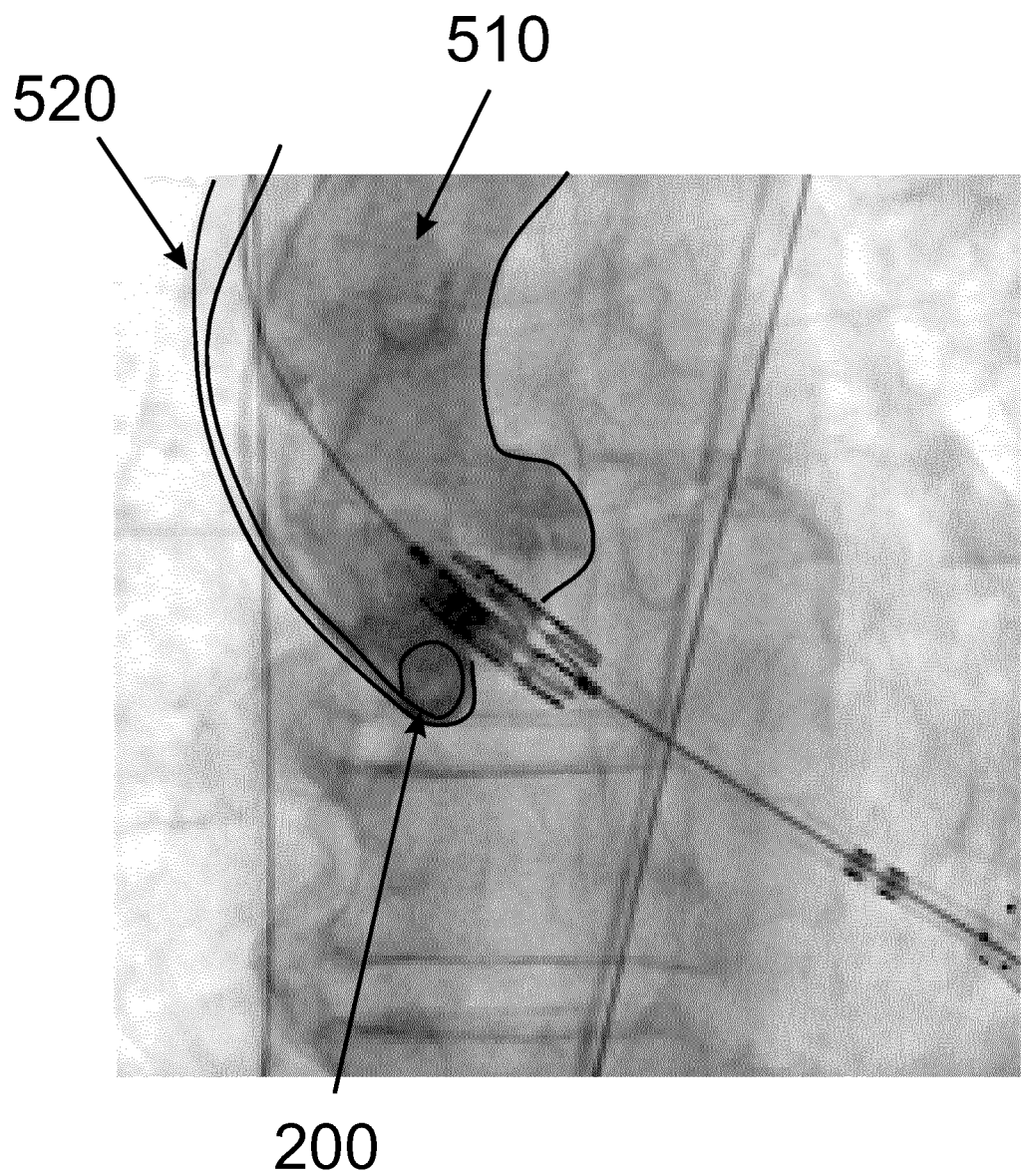
FIG. 4 shows an example of an angiographic image.

FIG. 4 shows an example of an angiography image including a darkened area 510 with a contrast agent in the ascending aorta. Based on such an angiography image, a roadmap 520 may be generated as outlines of the darkened area 510.

Figure 5:
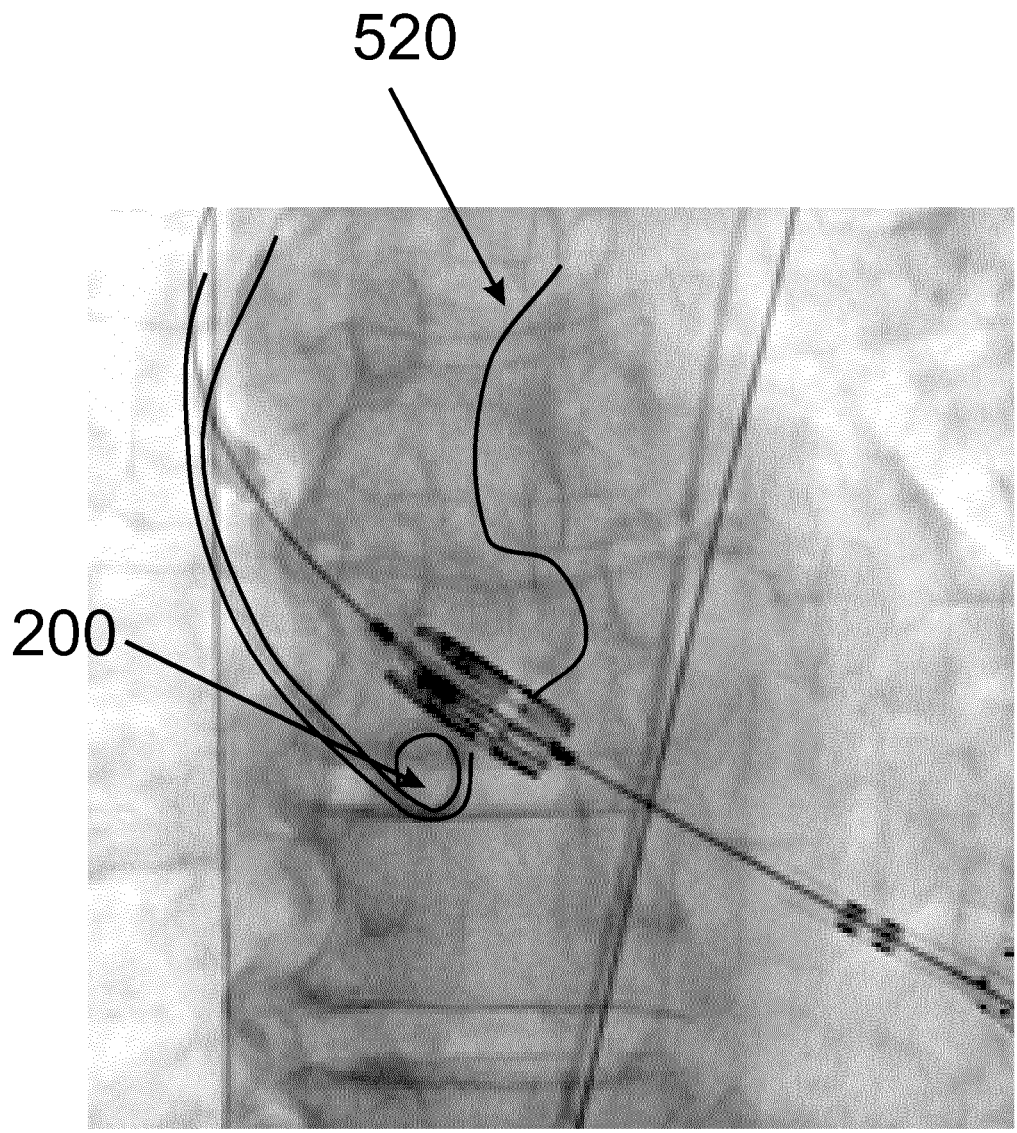
FIG. 5 shows an example of a fluoroscopic image with a roadmap.

FIG. 5 shows an example of a fluoroscopic image together with a roadmap as generated in step S1 of the above described method.

While the invention has been illustrated and described in detail in the drawings and afore-going description, such illustrations and descriptions are to be considered illustrative or exemplary and not restrictive, the invention is not limited to the disclosed embodiments.

Other variations to the disclosed embodiments can be understood and effected by those skilled in the art in practicing the claimed invention, from a study of the drawings, the disclosure and the appended claims. In the claims, the word 'comprising' does not exclude other elements or steps, and the indefinite article 'a' or 'an' does not exclude a plurality. A single processor or other unit may fulfill the functions of several items recited in the claims.

The mere fact that certain measures are recited and mutually different dependent claims does not indicate that a combination of these measured cannot be used to advantage. A computer program may be stored/distributed on a suitable medium such as an optical storage medium or a solid-state medium supplied together with or as a part of another hardware, but may also be distributed in other forms, such as via the internet or other wired or wireless telecommunication systems. Any reference signs in the claims should not be construed as limiting the scope.

LIST OF REFERENCE SIGNS 100 console
110 unit
120 device
200 instrument
220 tip portion of instrument
300 patient
400 x-ray device
420 x-ray source
430 C-arm
440 x-ray detector
460 table
500 landmark
510 darkened area
520 roadmap
600 processing unit
610 monitor
620 control device

The invention claimed is:

1. A method for automatic detection of an event in which a device is leaving a stable position relative to and within an anatomy, the method comprising the steps of:
   receiving a sequence of fluoroscopic images,
   detecting the device in at least two of the fluoroscopic images,
   determining a motion field of the detected device in the sequence of fluoroscopic images,
   generating a sequence of integrated images by integrating the sequence of fluoroscopic images taking into consideration the motion field,
   determining a saliency metric based on the integrated images, identifying a landmark in the integrated images based on the saliency metric, wherein said method further comprises the steps of:

visualizing at least one fluoroscopic image out of the sequence of fluoroscopic images together with a roadmap as an overlay of the roadmap on the at least one fluoroscopic image; and masking the roadmap when a motion of the landmark relative to the device is determined.

2. The method of claim 1, further comprising a step of:

determining as to whether the landmark is moving relative to the device, based on a variation of the saliency metric.

3. The method of claim 1, wherein the sequence of fluoroscopic images comprises a first fluoroscopic image and a second fluoroscopic image, wherein the determining of a motion field comprises a determining of a displacement of the device between a position detected in the first fluoroscopic image and a position detected in the second fluoroscopic image, and wherein the displacement is taken into consideration for integrating the plurality of fluoroscopic images.

4. The method of claim 1, wherein the integration of the sequence of fluoroscopic images is a temporal integration.

5. The method of claim 4, wherein the landmark in an integrated image is determined based on the height of pixel values.

6. The method of claim 5, wherein the saliency metric varies when pixel values vary in the sequence of integrated images.

7. The method of claim 1, wherein the landmark includes a calcification in a vascular system.

8. The method of claim 7, wherein the landmark includes an already implanted element.

9. A system for automatic detection of an event in which a device is leaving a stable position relative to and within an anatomy, comprising:

a device for generating fluoroscopic images, and a processing device for processing the fluoroscopy images in accordance with the method of claim 1.

10. The system of claim 9, further comprising a monitor for displaying images.

11. The system of claim 10, further comprising a database providing a roadmap.

12. A computer program for automatic detection of an event in which a device is leaving a stable position relative to and within an anatomy, when executed on a processing device of a system for automatic detection of an event in which a device is leaving a stable position relative to and within an anatomy, comprising:

a device for generating fluoroscopic images, and a processing device for processing the fluoroscopy images, causing the system to perform the method according to claim 1.

* * * * *